United States Patent [19]

Gewirtz et al.

[11] Patent Number: 5,472,944

[45] Date of Patent: Dec. 5, 1995

[54] SUPPRESSION OF MEGAKARYOCYTOPOIESIS BY NEUTROPHIL ACTIVATING PEPTIDE-2

[75] Inventors: Alan M. Gewirtz, Philadelphia; Mortimer Poncz, Wynnewood, both of Pa.

[73] Assignees: The University of Pennsylvania; Children's Hospital of Philadelphia, both of Philadelphia, Pa.

[21] Appl. No.: 173,264

[22] Filed: Dec. 27, 1993

Related U.S. Application Data

[63] Continuation of Ser. No. 792,990, Nov. 15, 1991, abandoned.
[51] Int. Cl.[6] .............................. A61K 38/00; C07K 5/00; C07K 7/00; A01N 37/18
[52] U.S. Cl. ............................... 514/12; 514/2; 530/300; 530/324
[58] Field of Search .......................... 514/12, 2; 530/300, 530/324

[56] References Cited

FOREIGN PATENT DOCUMENTS 9006321  6/1990  WIPO.

OTHER PUBLICATIONS

Baggiolini et al., Chem Abstract, vol. 114, No. 17, p. 606, Abst No. 114:162314e Apr. 29, 1991.
Walz et al., Chem. Abstr. vol. 117, p. 497 Abst. No. 117:24281c, 1992.
Holt et al., Chem Abst. vol. 116, Abst. No. 116:104136d, 1992.

Primary Examiner—Jill Warden
Assistant Examiner—A. M. Davenport
Attorney, Agent, or Firm—Seidel Gonda Lavorgna & Monaco

[57]  ABSTRACT

Neutrophil activating peptide-2 or analog thereof is administered to a mammal to achieve therapeutic reduction of the number of circulating platelets. The peptide is useful in treating essential thrombocythemia and reactive thrombocytosis.

6 Claims, 1 Drawing Sheet

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 70 amino acids
        ( B ) TYPE: amino acid
        ( C ) STRANDEDNESS: single stranded
        ( D ) TOPOLOGY: linear ( x i ) SEQUENCE DESCRIPTION: SEQ ID NO:1:

```
Ala  Glu  Leu  Arg  Cys  Met  Cys  Ile  Lys  Thr  Thr  Ser  Gly  Ile  His
                    5                        10                          15
Pro  Lys  Asn  Ile  Gln  Ser  Leu  Glu  Val  Ile  Gly  Lys  Gly  Thr  His
                    20                       25                          30
Cys  Asn  Gln  Val  Glu  Val  Ile  Ala  Thr  Leu  Lys  Asp  Gly  Arg  Lys
                    35                       40                          45
Ile  Cys  Leu  Asp  Pro  Asp  Ala  Pro  Arg  Ile  Lys  Lys  Ile  Val  Gln
                    50                       55                          60
Lys  Lys  Leu  Ala  Gly  Asp  Glu  Ser  Ala  Asp
                    65                       70
```

( 2 ) INFORMATION FOR SEQ ID NO:2:

( i ) SEQUENCE CHARACTERISTICS:
        ( A ) LENGTH: 36 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:2:

CCAGCCCCAT ATGGCTGAAC TCCGCTGCTG TATAAA    36

( 2 ) INFORMATION FOR SEQ ID NO:3:

( i ) SEQUENCE CHARACTERISTICS:
        ( A ) LENGTH: 37 Nucleotides
        ( B ) TYPE: nucleic acid
        ( C ) STRANDEDNESS: single stranded
        ( D ) TOPOLOGY: linear ( x i ) SEQUENCE DESCRIPTION: SEQ ID NO:3:

CCAGCCAAGC TTCCTGGGAG TTAAAGAAGT TTGGCAG    37

SUPPRESSION OF MEGAKARYOCYTOPOIESIS BY NEUTROPHIL ACTIVATING PEPTIDE-2

Reference to Government Grant

The invention was made with government support under grants CA 36896 and CA 01324 awarded by the National Institutes of Health. The government has certain rights in the invention. This is a continuation of application Ser. No. 07/792,990 filed on Nov. 15, 1991, and now abandoned.

FIELD OF THE INVENTION

The invention relates to the inhibition of megakaryocytopoiesis.

BACKGROUND OF THE INVENTION

Pluripotent hematopoietic stem cells are activated in the bone marrow to proliferate and differentiate into mature megakaryocytes, each of which is capable of releasing up to several thousand functional platelets in response to biological demand. Development of the stem cell proceeds by stages broadly corresponding to proliferation of progenitor cells, and differentiation of late progenitor and early precursor cells into mature megakaryocytes. Although regulation of this developmental process (megakaryocytopoiesis) is of substantial clinical interest for its potential application to disorders characterized by abnormal platelet production, endogenous factors responsible for stimulating or inhibiting proliferation and differentiation of megakaryocyte progenitor/precursor cells have not been thoroughly elaborated.

Thrombocytosis is a condition marked by the absolute increase in the number of circulating platelets. In some cases the elevation is acute and transient; in others it is chronic and persistent. The term "reactive thrombocytosis" has been commonly applied to define the concept that these patients have increased circulating platelet numbers in response to some underlying disease. This is in contrast to the condition where an autonomous drive to platelet production exists, commonly termed "thrombocythemia".

Reactive thrombocytosis may appear and persist as a result of chronic blood loss with iron deficiency, chronic inflammatory disease, chronic infectious disease, cancer and hemolytic anemia.

Primary thrombocythemia, also known as essential thrombocythemia, is an autonomous clonal proliferation of a pluripotent hematopoietic stem cell that results in an absolute increase in the number of circulating platelets. It shares several clinical features with other myeloproliferative disorders, most notably frequent bleeding and thrombotic lesions that represent major causes of morbidity and mortality.

Inhibitory factors capable of clinically significant megakaryocyte suppression have not been well-characterized. For example, both immunocytes and transforming growth factor-β (TGF-β) have been studied as potential inhibitors of megakaryocytopoiesis, with inconclusive results (see, e.g., *Blood* 67,479–483 and *Blood* 68,619–626, (1986)). Additionally, autoregulation via negative feedback mechanisms involving megakaryocyte products, including platelet-secreted 12–17kD glycoprotein, has been reported (*J. Cell Physiol.* 130, 361–368, (1987)). Platelet factor 4 and a synthetic C-terminal peptide have been shown to be capable of inhibiting megakaryocytopoiesis (Gewirtz et al., *J. Clin Invest.* 83, 1477–1486 (1989)). It has also been suggested that interferon-α and interferon-γ may have a role in regulating megakaryocyte colony formation (Ganser et al., *Blood* 70, 1173–1179 (1987); Chott et al., *Br. J. Haematol.* 74, 10–16 (1990)). While interferon-α has been used to lower platelet counts in patients with primary thrombocythemia and thrombocytosis associated with other types of malignant lesions, only approximately about 50% of patients achieve a stable state of remission. Moreover, on cessation of interferon therapy, recurrence of clinical and laboratory findings is usual (Gisslinger et al., *Lancet* 1, 634–637 (1989)).

While the potential utility of negative autocrine regulators or other megakaryocytopoiesis inhibitors in the clinical treatment of disorders characterized by excessively high platelet counts is apparent, none of the heretofore postulated inhibitors has so far proved useful in such applications.

Cytoreducive chemotherapeutic agents such as alkylating agents, radiophosporous and antimetabolites have been used to reduce platelet numbers. Most have leukemogenic potential. Their use has largely been abandoned in favor of hydroxyurea. However, hydroxyurea should at best be considered an agent with uncertain carcinogenic potential because at least one case of primary thrombocythemia conversion to acute leukemia has been linked to hydroxyurea therapy (Anker-Lugtenberg et al., *Am. J. Hematol.* 33:152 (1990)).

Anagrelide, a member of the imidazo(2,1-b)quinazolin-2-one series, is an investigational drug which has been recently proposed for the treatment of thrombocytosis. Anagrelide has been shown to be capable of controlling platelet counts in most patients suffering from essential thrombocythemia as a consequence of an underlying myeloproliferative disorder. Suppression of platelet counts by anagralide appears to be selective relative to changes in white blood cell count and hemoglobin. However, the drug's potent effect on inhibiting platelet activation requires further study.

SUMMARY OF THE INVENTION

A method for suppressing megakaryocytopoiesis in a mammal is provided, which results in the reduction of the number of circulating platelets in the bloodstream of that mammal. An effective amount of neutrophil activating peptide- 2 (NAP-2) or analog thereof is administered to effect such platelet reduction. The invention is particularly useful in the treatment of disorders characterized by an excessively high platelet count. NAP-2 suppresses megakaryocyte maturation (i.e., differentiation). We have found that the inhibitory effect of NAP-2 is lineage-specific, since at the highest doses tested, NAP-2 caused no significant inhibition of either colony forming units-granulocyte macrophage (CFU-GM) or burst forming units-erythrocyte (BFU-E) .

By "analog" with respect to NAP-2 is meant a modified polypeptide having an amino acid sequence substantially the same as that of NAP-2 in which one or more amino acids have been deleted or substituted, or in which one or more amino acids have been inserted; which modified polypeptide retains the property of inhibiting megakaryocytopoiesis.

DETAILED DESCRIPTION OF THE INVENTION

Figure 1:
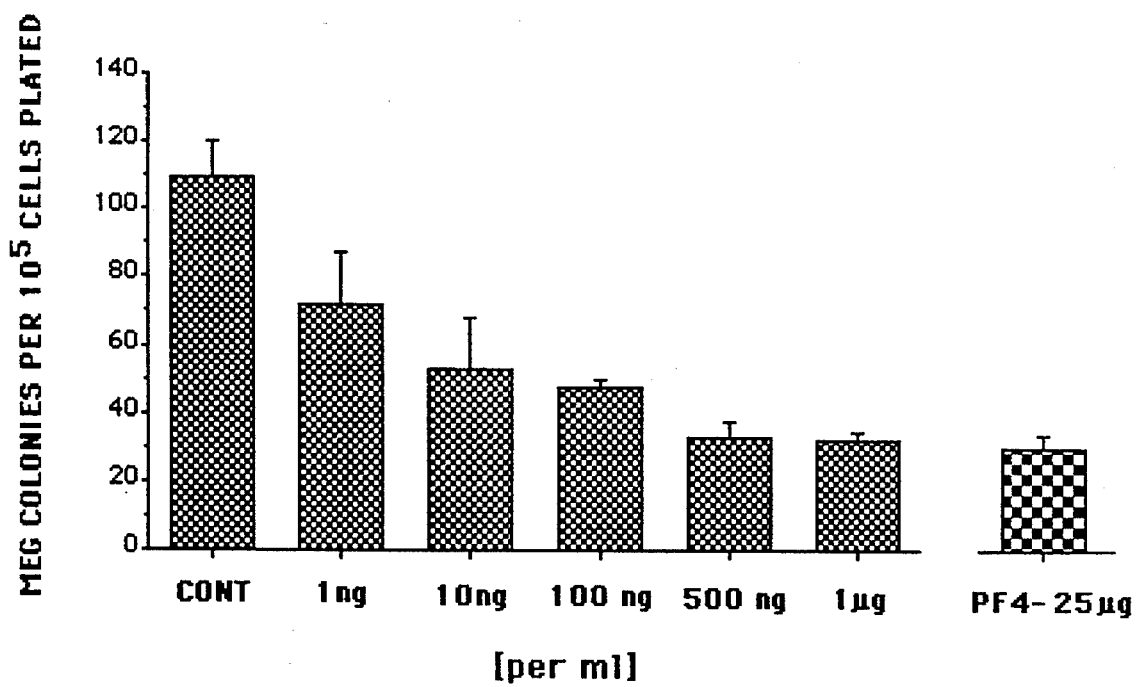
FIG. 1 is a graph of the effect of neutrophil activating peptide-2 on megakaryocyte colony formation at concentrations of 0 (CONT), 1, 10, 100, 500 and 1000 ng/ml. For comparison purposes, the effect of platelet factor 4 (PF4) at 25 µg/ml is also shown.

According to the invention, NAP-2, or analog thereof, is employed to inhibit megakaryocytopoiesis to effect in vivo reduction of platelet numbers. Sufficient NAP-2 is given, preferably by intravenous administration, to decrease the number of circulating platelets. Depending upon the route of administration and idiosyncratic factors, most particularly individual platelet count and the rate of NAP-2 peptide clearance, the average dosage may be as little as about 2.5 mg per day, up to several grams per day, for a human subject.

Prior to the present invention, NAP-2 was known only as a potent neutrophil activating agent produced by the cathepsin D-mediated cleavage of the eleven $NH_2$-terminal amino acids of β-thromboglobulin. NAP-2 may also be generated by cleavage of two inactive precursors, connective-tissue-activating peptide III (CTAP-III) and platelet basic protein (PRP), which are stored in the s-granules of blood platelets (Car et al., *Biochem J.* 275, 581–584 (1991)).

The amino acid sequence of NAP-2 is known and reported, and reproduced herein (SEQUENCE ID NO:1). Also see Clark-Lewis et al., *Biochemistry* 30, 3128–3135 (1991), the entire disclosure of which is incorporated herein by reference. The complete 70-amino acid protein, and megakaryocytopoiesis-inhibiting analogs thereof, may be chemically synthesized by conventional solid phase synthetic techniques initially described by Merrifield, in *J. Am. Chem. Soc.* 15, 2149–2154 (1963). Other peptide synthesis techniques may be found, for example, in M. Bodanszky et al., *Peptide Synthesis,* John Wiley & Sons, 2d Ed. (1976) as well as in other reference works known to those skilled in the art. A summary of peptide synthesis techniques may be found in J. Stuart and J. D. Young, *Solid Phase Peptide Synthesis,* Pierce Chemical Company, Rockford, Ill. (1984). The synthesis of peptides by solution methods may also be used, as described in *The Proteins.,* vol- II, 3d Ed., Neurath, H. et al., Eds., p. 105–237, Academic Press, New York, N.Y. (1976). Appropriate protective groups for use in such syntheses will be found in the above texts as well as in J. F. W. McOmie, *Protective Groups in Organic Chemistry,* Plenum Press, New York, N.Y. (1973).

In general, these synthetic methods involve the sequential addition of one or more amino acid residues or suitably protected amino acid residues to a growing peptide chain. Normally, either the amino or carboxyl group of the first amino acid residue is protected by a suitable, selectively-removable protecting group. A different, selectively-removable protecting group is utilized for amino acids containing a reactive side group, such as lysine.

NAP-2 has been prepared in 99% purity from $N^{\alpha}$-tertbutyloxycarbonyl(t-Boc)-amino acids by automated solid-phase methods (Clark-Lewis et al., *Biochemistry* 30, 3128–3135 (1991)).

Since the amino acid sequence of NAP-2 is known, it may of course also be prepared by recombinant DNA techniques well-known to those skilled in the art. Moreover, analogs involving the substitution, deletion or insertion of one or more amino acids may similarly be prepared by such recombinant techniques, or by solid or liquid phase peptide syntheses, as described above.

It is contemplated, based upon the available 70-amino acid sequence of NAP-2 (SEQUENCE ID NO:1), that analogs of NAP-2 may be prepared and effectively screened for ability to inhibit megarkaryocytopoiesis according to the megakaryocyte assay hereinafter described. In particular, it is contemplated that conservative amino acid changes may be made which do not alter the biological function of the peptide. For instance, one polar amino acid, such as glycine, may be substituted for another polar amino acid; or one acidic amino acid, such as aspartic acid may be substituted for another acidic amino acid, such as glutamic acid; or a basic amino acid, such as lysine, arginine or histidine may be substituted for another basic amino acid; or a nonpolar amino acid, such as alanine, leucine or isoleucine may be substituted for another non-polar amino acid.

The degree of homology between the NAP-2 analog and native NAP-2 is preferably at least 80%, more preferably at least 90%, most preferably at least 95%.

NAP-2 or NAP-2 analog is contemplated for use according to the invention in lowering blood levels of circulating platelets as deemed clinically advantageous, and for use in reducing the ability of these platelets to support blood clot formation. Pathological vascular reactions associated with excessively high platelet counts include stroke, pulmonary emboli, and related thromboembolic complications. A predisposing factor of these potentially fatal complications, high circulating platelet levels, may be substantially minimized by NAP-2. The invention is of particular clinical relevance in the treatment of myeloproliferative and other disorders characterized by clinically disadvantageous high platelet counts. Treatment of such disorders is accomplished according to the practice of the invention by the administration of NAP-2 or NAP-2 analog in sufficient quantities to suppress platelet production and approach normal hemostasis, as measured by significant reduction in platelet count of at least about 10%.

NAP-2 or NAP-2 analog may be administered by any convenient route which will result in the delivery to the bloodstream of a megakaryocytopoiesis-inhibiting effective amount. Contemplated routes of administration include parenteral and oral routes. Generally, the peptide may be administered in an amount sufficient to provide a blood plasma concentration of between about 10 and about 500 ng/ml, more preferably from about 20 to about 100 ng/ml. Plasma concentrations higher or lower than this may be utilized, depending on the nature of the treatment. Therapeutic dosages, based upon a 70 kg body weight, may range from about 0.1 mg to several grams per day. Preferably, the dosage ranges form about 0.1 to about 500 mg per day, most preferably from about 0.5 to about 50 mg per day.

For parenteral administration, NAP-2 or analog thereof may be given in any of the known pharmaceutical carriers useful for delivering polypeptide drugs. The carrier will typically comprise sterile water, although other ingredients to aid solubility or for preservation purposes may be included. Injectable suspensions may also be prepared in which appropriate liquid carriers, suspending agents and the like may be employed. The parenteral routes of administration may comprise intravenous injection, intramuscular injection or subcutaneous injection, with intravenous injection being preferred.

For intravenous administration, the peptide may be dissolved in an appropriate intravenous delivery vehicle containing physiologically compatible substances such as NaCl, glycine and the like, having a buffered pH compatible with physiologic conditions. Such intravenous delivery vehicles are known to those skilled in the art.

NAP-2 or analog thereof may be operatively linked to a pharmaceutically acceptable carrier molecule to form a megakaryocytopoiesis-inhibiting complex. By "operatively linked" is meant any form of chemical or physical association or bond, including, but not limited to non-covalent complex formation, covalent bonding (including but not limited to covalent bonding by one or more cross-linking agents), and the like, which does not substantially interfere with the megakaryocytopoiesis-inhibiting activity of NAP-2.

Typically, the molecule carrier will comprise a protein, such as albumin, to improve the delivery of NAP-2 and/or prolonging the half-life of NAP-2 in the body. Techniques for protein conjugation through activated functional groups are particularly applicable. For a review of such techniques, see Aurameas et al., *Scan. J. Immunol,* 8, Supp. 1, 7–23 (1978). Also see U.S. Pat. Nos. 4,493,795 and 4,671,958. A wide range of homobifunctional and heterobifunctional cross-linking agents for covalently linking proteins are well known to those skilled in the art. For a partial list of such agents, see international patent application WO 90/14102 (1990), p. 29–31. Also included in the scope of such associations is the formation of a unitary protein by genetic engineering, resulting from the co-expression of genetic information for all or part of NAP-2 and the carrier molecule as a single protein.

According to an exemplary treatment protocol, 2.5 mg NAP-2 or NAP-2 analog of generally equivalent potency is administered intravenously to a 70 kg patient having distal ischemia, stroke, or other thromboembolic phenomena associated with abnormally elevated platelet count. The platelet count and function are monitored from seven to ten days after administration by analysis of blood samples taken at 4-hour intervals to evaluate NAP-2 potency and clearance rates. At the end of the evaluation period, the dosage is adjusted as necessary to establish an improved platelet count or function, and the patient is again monitored once or twice weekly, as described. At the end of the period, the NAP-2 dosage is again adjusted as necessary, with repetition of the described monitoring and evaluation procedure until the platelet count is substantially stabilized at a normal or near-normal level. The dosage required to obtain the desired stabilized platelet count comprises a therapeutic dosage according to the present invention. Indefinite daily administration of the therapeutic dosage may be necessary in order to maintain normal platelet levels during chronic thrombocytosis.

The practice of the invention is illustrated by the following non-limiting example.

EXAMPLE

A. Preparation of NAP-2

NAP-2 was made using the expression vector pT7-7 (Brookhaven National Laboratory) with the appropriate insert, and purified as previously described for recombinant platelet factor 4 (Park et al., *Blood* 75, 1290–1295 (1990)).

Accordingly, the appropriate insert was prepared by polymerase chain reaction (PCR) from the 700 base pair β-thromboglobulin cDNA (Walz and Baggiolini, *Biochem. Biophys Res. Comm.* 159, 969–975 (1989)) isolated from a Dami cell expression cDNA library. The forward PCR primer CCAGCCCCAT ATGGCTGAAC TCCGCTGCTG TATAAA (SEQ ID NO:2) encodes an additional methionine residue in front of the known start of the NAP-2 N-terminus (Majumdar et al., *J. Biol. Chem.* 266, 5785–5789 (1991)). The primer also had an Nde I site inserted into it. The reverse PCR primer CCAGCCAAGC TTCCTGGGAG TTAAA-GAAGTT TGGCAG (SEQUENCE ID NO:3) is from the β-thromboglobulin cDNA 3'-untranslated region and has a Hind III site engineered into it. PCR amplification was performed according to standard techniques. The insert was cut with Nde I/Hind III and ligated into the pT7-7 vector, which was digested according to the same approach. Following sequence confirmation of the construct, the NAP-2 expression vector was subcloned into *E. coli* BL1(DE3)pLysS (Brookhaven National Laboratory).

A positive clone was identified and used to grow 1 L of the bacteria in Luria broth containing 50 µg/ml ampicillin and 50 µg/ml chloramphenicol until the optical density at 600 nm reached 0.600 (37° C.). Isopropylthio-β-D-galactoside was then added to a concentration of 1 mM, and the bacteria was grown for an additional 3 hours at 37° C. As previously described (Park et al., supra) the bacteria was spun down and then resuspended in a buffer comprising Tris-HCl, pH 8.0 and 50mM NaCl ("TE$^{-50}$") with 0.5% sodium deoxycholate, 1% Triton X-100, 5 mg/ml lysozyme and 1 mM phenylmethylsulfonyl fluoride. After 1 hour at 4° C., the bacteria were sonicated to release the protein. The bacterial debris was removed by centrifugation. The protein was bound to heparin agarose in TE$^{50}$ overnight at 4° C. After washing the column with TE$^{150}$, (same as TE$^{50}$, but including 150 mM NaCL in lieu of 50 mm NaCl), the NAP-2 protein was eluted with TE$^{500}$. After two rounds of heparin agarose purification, the NAP-2 was concentrated using a DIAFLO YM3 filter (W. R. Grace & CO., Beverly, Mass.) and switched from the TE$^{500}$ buffer to 0.1% trifluoroacetic acid. The NAP-2 was further purified using high performance liquid chromatography using a C18 column and a gradient of trifluoroacetic acid and acetonitrile.

The identity of the NAP-2 protein was confirmed by Edman degradation sequencing. Sequencing demonstrated the N-terminus initiating methionine residue had been removed, such that the recombinant NAP-2 thus prepared was identical in amino acid sequence to the corresponding native protein. The purity of the sample was confirmed by Coomasie blue staining and immunoblotting.

B. Megakaryocyte Colony Assay

The ability of NAP-2 to inhibit megakaryocyte colony formation was demonstrated by the following assay.

Megakaryocyte colonies were cloned in plasma clot cultures as previously described (*Blood* 61, 384–9 (1983)). The cell population cultured consisted of either unseparated high density marrow mononuclear cells (MNC), or MNC depleted of adherent monocyte-macrophages and T lymphocytes using methods previously reported (*J. Immunol.* 139, 2915–2925 (1987)). To estimate basal growth conditions in marrow, the cultures contained no exogenous source of growth factors. To provide such essential growth factors, all cultures were supplemented with normal human AB serum (30% v/v) derived from the platelet-poor plasma of a single donor. Various amounts of pure recombinant NAP-2 were added to the unseparated marrow MNC.

Megakaryocyte colonies were enumerated by indirect immunofluorescence assay utilizing a rabbit anti-human platelet glycoprotein antiserum as a megakaryocyte probe (ibid.). The antiserum used was highly specific for recognition of platelet glycoproteins. It does not recognize monocytes. A cluster of three or more intensely fluorescent cells was counted as one colony. The aggregate results of five such experiments are shown in FIG. 1.

NAP-2 displayed a potent anti-megakaryocytopoiesis activity, causing 44%, 52%, 57%, 70% and 70% reduction in colony formation in comparison to controls (109±12 colonies per $10^5$ cells) at concentrations of 1, 10, 100, 500 and 1000 ng/ml (p<0.001 at all doses). In the same assay, recombinant platelet factor 4, another inhibitor of megakaryocytopoiesis, was most active at concentrations greater than 10 μg/ml.

The effect of NAP-2 inhibition of megakaryocytopoiesis was lineage-specific since at the highest dose tested, NAP-2 caused no significant inhibition of CFU-GM or BFU-E (data not shown).

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indicating the scope of the invention.

We claim:

1. A method for reducing the number of circulating platelets in the bloodstream of a mammal comprising administering to the mammal an amount of neutrophil activating peptide-2 effective to induce such a reduction.

2. A method according to claim 1 wherein the amount of neutrophil activating peptide-2 administered is sufficient to reduce the number of circulating platelets by at least about 10%.

3. A method according to claim 1 for treatment of thrombocytosis comprising administering to a human being a daily dosage of neutrophil activating peptide-2 of from about 0.1 to about 500 mg.

4. A method according to claim 3 wherein the daily dosage is from about 0.5 to about 50 mg.

5. A method for reducing the number of circulating platelets in the bloodstream of a mammal comprising administering to the mammal a platelet number-reducing effective amount of a conjugate comprising neutrophil-activating peptide-2 operatively linked to a pharmaceutically acceptable carrier molecule.

6. A method acdording to claim 5 wherein the carrier molecule comprises a protein.

* * * * *